United States Patent
Ward et al.

(10) Patent No.: US 9,061,115 B2
(45) Date of Patent: Jun. 23, 2015

(54) METHODS AND APPARATUS FOR PROVIDING AN ARTERIOVENOUS FISTULA

(71) Applicant: Medtronic Vascular, Inc., Santa Rosa, CA (US)

(72) Inventors: Sean Ward, Castleknock (IE); Aram Jamous, Oranmore (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 204 days.

(21) Appl. No.: 13/711,335

(22) Filed: Dec. 11, 2012

(65) Prior Publication Data
US 2013/0116614 A1   May 9, 2013

Related U.S. Application Data

(62) Division of application No. 12/691,806, filed on Jan. 22, 2010, now abandoned.

(51) Int. Cl.
| | |
|---|---|
| *A61F 2/06* | (2013.01) |
| *A61M 27/00* | (2006.01) |
| *A61B 17/11* | (2006.01) |
| *A61M 1/36* | (2006.01) |
| *A61M 3/02* | (2006.01) |
| *A61B 17/068* | (2006.01) |

(Continued)

(52) U.S. Cl.
CPC ............ *A61M 27/002* (2013.01); *A61B 17/068* (2013.01); *A61B 17/11* (2013.01); *A61B 2017/00862* (2013.01); *A61B 2017/00867* (2013.01); *A61B 2017/0649* (2013.01); *A61B 2017/1107* (2013.01); *A61B 2017/1139* (2013.01); *A61F 2/064* (2013.01); *A61M 1/3655* (2013.01); *A61M 3/0262* (2013.01); *A61M 3/0279* (2013.01)

(58) Field of Classification Search
CPC ........... A61B 17/11; A61B 2017/0649; A61B 2017/1139; A61B 2017/1107; A61M 27/002; A61M 1/3655; A61M 3/0279; A61F 2/064
USPC ..................... 623/1.11; 604/8, 9, 10
See application file for complete search history.

(56) References Cited

U.S. PATENT DOCUMENTS

| | | | |
|---|---|---|---|
| 5,304,220 A * | 4/1994 | Maginot | ........................ 128/898 |
| 5,407,427 A | 4/1995 | Zhu et al. | |
| 5,695,462 A | 12/1997 | Sutcu | |

(Continued)

OTHER PUBLICATIONS

Faul et al., "Percutaneous Creation of Arteriovenous Shunts" Vascular Disease Management, vol. 5, Sep. 1, 2008.

*Primary Examiner* — Tuan V Nguyen
*Assistant Examiner* — Chima Igboko

(57) ABSTRACT

Methods and apparatus for creating an artificial arteriovenous fistula between an artery and an adjacent vein are disclosed. Methods include utilizing a hollow spiral shunt that defines a fluid passageway between a proximal port and a distal port thereof. The spiral shunt is loaded within a delivery device that is transversely advanced through a wall of the artery. A piercing end of the spiral shunt is than exposed and the delivery device is rotated to pierce an opposing wall of the artery and a wall of the adjacent vein with the spiral shunt piercing end. Rotation of the delivery device corkscrews the spiral shunt through the walls of the artery and the vein in order to position the spiral shunt to fluidly connect the artery and vein. Once so positioned, the spiral shunt is released to be deployed between the artery and vein lumens thereby forming an artificial arteriovenous fistula therebetween.

11 Claims, 5 Drawing Sheets

(51) Int. Cl.
*A61B 17/00* (2006.01)
*A61B 17/064* (2006.01)

(56) References Cited

U.S. PATENT DOCUMENTS

| | | | | |
|---|---|---|---|---|
| 5,702,412 A * | 12/1997 | Popov et al. | | 606/159 |
| 6,283,951 B1 * | 9/2001 | Flaherty et al. | | 604/529 |
| 6,375,615 B1 * | 4/2002 | Flaherty et al. | | 600/439 |
| 6,616,675 B1 * | 9/2003 | Evard et al. | | 606/155 |
| 6,626,917 B1 | 9/2003 | Craig | | |
| 6,638,237 B1 * | 10/2003 | Guiles et al. | | 604/8 |
| 6,726,677 B1 * | 4/2004 | Flaherty et al. | | 604/528 |
| 6,837,893 B2 | 1/2005 | Miller | | |
| 6,949,080 B2 | 9/2005 | Wolf et al. | | |
| 7,033,372 B1 | 4/2006 | Cahalan | | |
| 7,618,427 B2 * | 11/2009 | Ortiz et al. | | 606/142 |
| 8,409,224 B2 * | 4/2013 | Shriver | | 606/144 |
| 8,454,632 B2 * | 6/2013 | Binmoeller et al. | | 606/151 |
| 2002/0183786 A1 | 12/2002 | Girton | | |
| 2003/0138890 A1 * | 7/2003 | Glucksmann et al. | | 435/69.1 |
| 2004/0193262 A1 * | 9/2004 | Shadduck | | 623/4.1 |
| 2004/0220596 A1 | 11/2004 | Frazier et al. | | |
| 2005/0107733 A1 | 5/2005 | Faul et al. | | |
| 2005/0113631 A1 * | 5/2005 | Bolling et al. | | 600/16 |
| 2005/0165427 A1 * | 7/2005 | Jahns et al. | | 606/153 |
| 2005/0203551 A1 * | 9/2005 | Weadock et al. | | 606/153 |
| 2006/0025790 A1 * | 2/2006 | de Winter et al. | | 606/153 |
| 2006/0036267 A1 * | 2/2006 | Saadat et al. | | 606/153 |
| 2007/0299384 A1 * | 12/2007 | Faul et al. | | 604/8 |
| 2008/0132999 A1 * | 6/2008 | Mericle et al. | | 623/1.34 |
| 2008/0306580 A1 * | 12/2008 | Jenson et al. | | 623/1.11 |
| 2009/0099578 A1 | 4/2009 | Heneveld | | |
| 2009/0143713 A1 * | 6/2009 | Van Dam et al. | | 604/9 |
| 2009/0156978 A1 | 6/2009 | Faul et al. | | |
| 2009/0297635 A1 * | 12/2009 | Sheth | | 424/722 |
| 2010/0022940 A1 * | 1/2010 | Thompson | | 604/9 |
| 2010/0174281 A1 * | 7/2010 | Jahns et al. | | 606/33 |
| 2011/0295055 A1 * | 12/2011 | Albrecht et al. | | 600/37 |

* cited by examiner

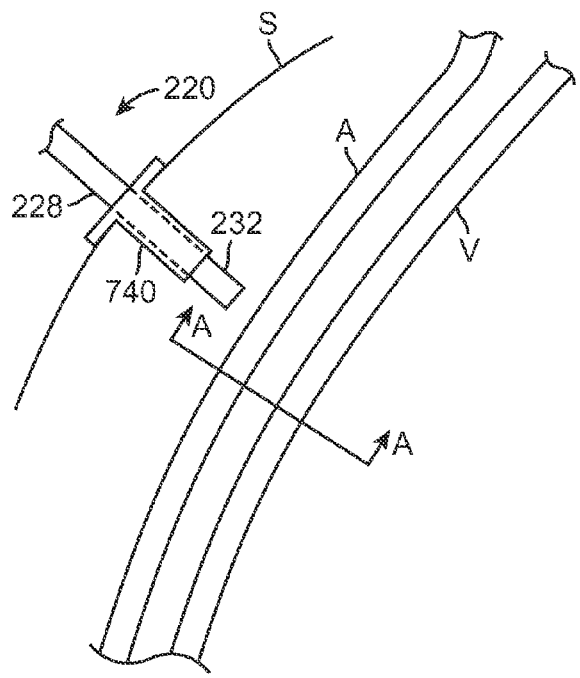
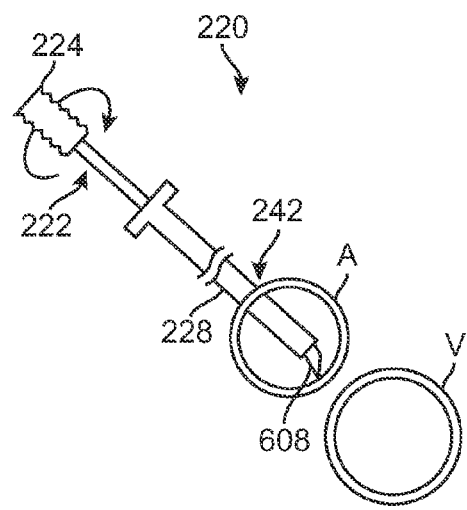
FIG. 7  FIG. 8
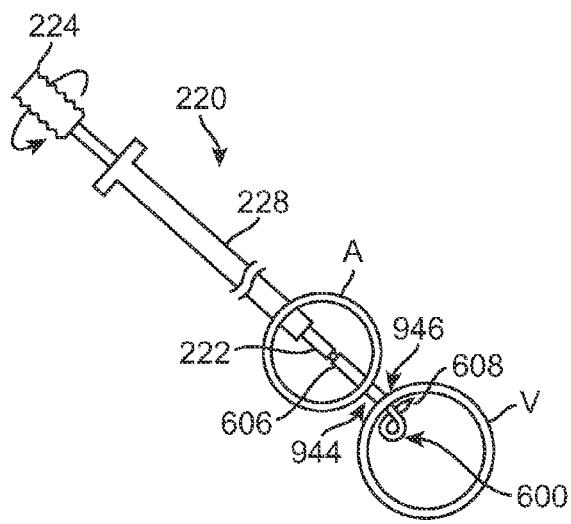
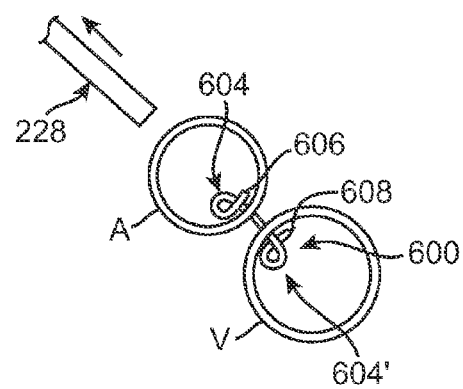
FIG. 9  FIG. 10

METHODS AND APPARATUS FOR PROVIDING AN ARTERIOVENOUS FISTULA

CROSS-REFERENCE TO RELATED APPLICATIONS

This application is a division of U.S. application Ser. No. 12/691,806, filed on Jan. 22, 2010, the entirety of which is hereby incorporated by reference.

FIELD OF THE INVENTION

The present invention relates to implanted medical devices. In particular, the present invention relates to an arteriovenous shunt and methods for creating an artificial fistula between adjacent blood vessels.

BACKGROUND OF THE INVENTION

Chronic obstructive pulmonary disease (COPD), also called chronic obstructive airway disease, is a syndrome that may be caused by a number of different diseases, all of which damage the alveoli and bronchioles, leading to impaired lung function. These diseases include asthmatic bronchitis, chronic bronchitis (with normal airflow), chronic obstructive bronchitis, bullous disease, and emphysema. As the alveoli and bronchial tubes are destroyed, the remaining healthy lung tissue must work harder to provide the required amount of blood oxygenation. The need for more air leads to lung over-inflation. As the lung over-expands, it gradually enlarges, completely filling the chest cavity and causing a sense of shortness of breath. The lung eventually loses its elasticity and the combination of a larger, less elastic lung and damaged, nonfunctioning tissue leads to slower airflow into and out of the lung, resulting in the feeling in the patient of an obstructed airway.

One manner of treating COPD is oxygen therapy, which requires a patient to remain near a stationary oxygen source or carry a bulky portable oxygen source when away from home or a treatment facility. Understandably such oxygen therapy has many disadvantages. One surgical treatment that has been proposed for treating patients with COPD is lung reduction surgery. Such surgery, however, can be used on only a small percentage of the total patient population, requires long recovery times, and does not always provide a clear patient benefit.

Arteriovenous (AV) shunt devices have been proposed for treating COPD by providing a fistula between an artery and a vein that are anatomically parallel to each other. The shunt allows oxygen-rich blood from the artery to flow to the vein and thereby increases the oxygen content of the blood returning to the heart and lungs, which in turn is considered to benefit a patient suffering from COPD. Such shunt devices have been suggested to be implanted via an open surgical procedure, a minimally invasive surgical procedure and an intravascular procedure depending on the specific arterial and venous locations that are to be connected by the AV shunt. However, a need continues to exist in the art for an AV shunt that may be quickly and simply delivered and deployed via a minimally invasive procedure. Accordingly apparatus and methods for treating patients suffering from COPD and other related conditions by deploying a shunt in a minimally invasive procedure to create a fistula between adjacent vascular structures are provided herein.

BRIEF SUMMARY OF THE INVENTION

Embodiments hereof are directed to methods and apparatus for creating an artificial arteriovenous fistula between an artery and an adjacent vein. A method in accordance herewith includes utilizing a hollow spiral shunt that defines a fluid passageway between a proximal port and a distal port thereof. The spiral shunt is loaded within a distal end of a delivery device and the distal end of the delivery device is transversely advanced through a wall of the artery into an arterial lumen. The delivery device is than manipulated to expose at least a piercing end of the spiral shunt within the lumen of the artery. The spiral shunt is distally advanced and rotated to pierce an opposing wall of the artery and a wall of the adjacent vein with the piercing end of the spiral shunt. Rotation of the spiral shunt corkscrews the spiral shunt through the walls of the artery and the vein in order to position the spiral shunt to fluidly connect the artery and vein. Once so positioned, the spiral shunt is released from the delivery device such that the spiral shunt is deployed with its proximal port within the artery lumen and its distal port within the vein lumen to form the artificial arteriovenous fistula between the artery and vein, which allows blood flow from the artery to the vein via the spiral shunt's fluid passageway.

The spiral shunt may be loaded within the delivery device by screwing the spiral shunt onto a push rod component of the delivery device. The push rod component may be slidably received within a tubular sheath of the delivery device such that sliding the tubular sheath relative to the push rod component positions the spiral shunt within the distal end of the delivery device. In such an arrangement, the spiral shunt is held in a straightened configuration within the tubular sheath of the delivery device and returns to its preset spiral configuration upon release from the tubular sheath.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 7-10 illustrate a method of creating an artificial arteriovenous fistula between an artery and an adjacent vein with the shunt of FIG. 6 in accordance with an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of arteriovenous shunting procedures, the invention may also be used between any other body passageways where it is deemed useful. Furthermore, there is no intention to be bound by any expressed or implied theory presented in the preceding technical field, background, brief summary or the following detailed description.

Figure 1:
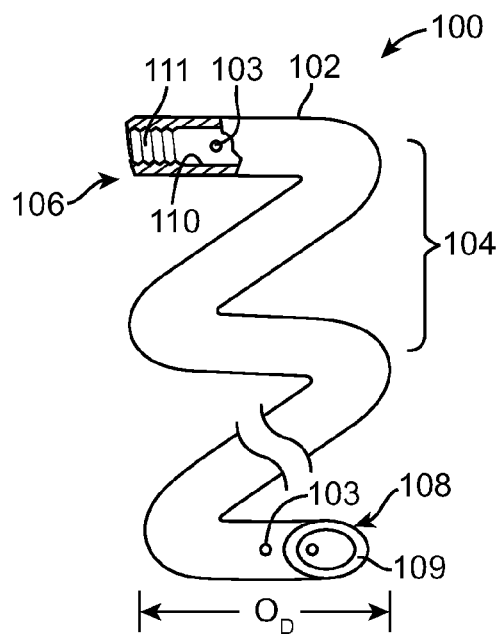
FIG. 1 is a partial sectional view of an arteriovenous shunt in accordance with an embodiment hereof.

FIG. 1 is a partial sectional view of an arteriovenous shunt 100 in accordance with an embodiment hereof. Shunt 100 is formed from a resilient hollow tube 102 shaped into a spiral or helical configuration having a series of windings or turns 104. A single winding 104 of shunt 100 may also be described mathematically as a helical torus wherein the generally toroidal or "doughnut" shape is formed out of plane by one turn of a helix. Windings 104 of shunt 100 have a longitudinally-extending cylindrical profile, which in embodiments hereof may have an outside diameter $O_D$ of between 2 mm to 7 mm. In various embodiments, shunt 100 may have between two to six windings or turns 104 with more or less spacing between consecutive turns than shown in the embodiment of FIG. 1. For example in the embodiment shown in FIGS. 6 and 6A, shunt 600 is formed from a resilient hollow tube 602 shaped into a spiral or helix having two and a half turns 604 with an attachment end 606 being aligned with a longitudinal axis La of shunt 600, as discussed further below.

Hollow tube 102 of shunt 100 has an attachment end 106 and a piercing end 108, and defines a fluid passageway 110 that extends therebetween. As such attachment and piercing ends 106, 108 define proximal and distal fluid ports, respectively, of shunt fluid passageway 110. In an embodiment, one or more side fluid ports 103 may be included proximate attachment end/proximal fluid port 106 and/or piercing end/distal fluid port 108 to facilitate fluid movement into and out of shunt fluid passageway 110. Such side fluid ports 103 may be particularly useful if terminal fluid ports 106 or 108 are blocked, as by inadvertently abutting against a vessel wall. Attachment end 106 of shunt 100 has internal screw threads 111 for mating with external screw threads 523 of a push rod 222 of a delivery system 220, as shown and described with reference to FIGS. 2-5. Piercing end 108 of shunt 100 has a non-coring sharpened point 109, which in an embodiment includes a double grind cut, in order to pierce a wall of a vessel without coring, i.e., without removing vessel tissue. In an embodiment, an inclined face of piercing end 108 of shunt 100 may be angled with respect to the longitudinal axis of fluid passageway 110 in order to reduce or prevent tissue coring during insertion of shunt 100 into the wall of the vessel. In an embodiment, the inclined face of piercing end 108 may be ground at an angle of between 10° to 15° to the longitudinal axis of fluid passageway 110 whereby tissue coring during shunt insertion may be substantially prevented. In various embodiments, hollow tube 102 has a wall thickness in the range of 0.1 mm to 0.3 mm with fluid passageway 110 having a diameter ranging from 0.5 mm to 5 mm.

Hollow tube 102 of shunt 100 is formed from a biocompatible material that permits shunt 100 to be substantially straightened for delivery to the treatment site, as shown and described with reference to FIG. 2, and that returns shunt 100 to its preset spiral form depicted in FIG. 1 upon deployment in vivo. Thus "resilient" as used herein to refer to hollow tube 102 means a tube elastically capable of resuming an original set shape or form after being straightened, deformed, compressed, or the like. In an embodiment, hollow tube 102 of shunt 100 may be formed of a biocompatible resilient metal such as spring temper stainless steel, a Co—Ni—Cr—Mo super alloy, or NiTi alloys such as nitinol, which utilize the pseudo-elastic properties of stress induced martensite.

Figure 2:
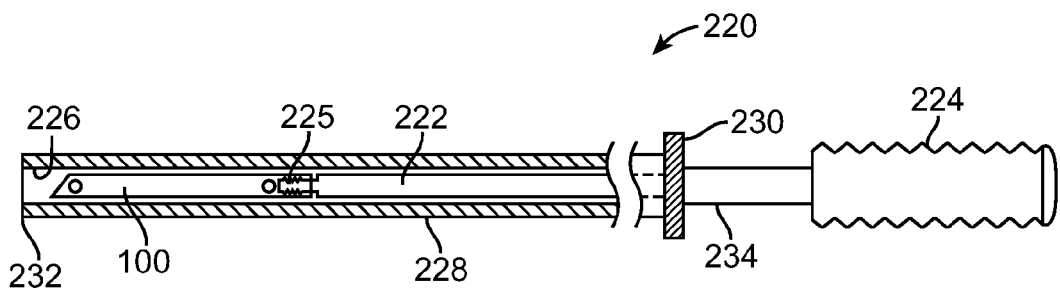
FIG. 2 is a partial sectional view of a delivery system in accordance with an embodiment hereof with the arteriovenous shunt of FIG. 1 held in a straightened delivery configuration therein.

FIG. 2 is a partial sectional view of a delivery system 220 in accordance with an embodiment hereof with arteriovenous shunt 100 of FIG. 1 held in a straightened delivery configuration therein. Delivery system 220 includes push rod 222 that has a handle 224 attached to a proximal end of a shaft portion 234 for manipulation by a clinician. In embodiments hereof, shaft portion 234 of push rod 222 may be a solid rod or core wire made from stainless steel, or other biocompatible metals with suitable mechanical properties with an outer diameter of between, e.g., 2 mm to 7 mm. In another embodiment shown and described in more detail with reference to FIG. 11, push rod 1122 may be formed from a hollow tube defining a lumen 1136 with an outer diameter of between, e.g., 2 mm to 7 mm and an inner diameter sized for slidably receiving a guidewire 1138 and/or a dilator 1139 therethrough.

Push rod 222 has at least a distal portion that slidably extends within a lumen 226 defined by an outer or tubular sheath 228. Outer sheath 228 has a proximal end 230 and a distal end 232 with an elongated tubular body defining lumen 226 therebetween. Outer sheath proximal end 230 extends proximally outside of the patient's body for manipulation by the clinician. In an embodiment, a locking mechanism may be positioned about proximal end 230 of outer sheath 228 to secure or hold outer sheath 228 and push rod 222 together to ensure that there is no premature longitudinal movement of push rod 222 relative to outer sheath 228 prior to delivery system 220 being located at a treatment site. In an embodiment, the locking mechanism may be a rotating collet that is positioned about outer sheath 228 to compress outer sheath 228 into contact with push rod 222 when rotated to thereby "lock" the components together. Shunt 100 is connected to a distal end 225 of push rod 222 by a screw thread arrangement and is held in the straightened configuration within lumen 226 by outer sheath 228. Outer sheath 228 is formed from hollow tubing that has sufficient stiffness to maintain shunt 100 in the straightened configuration until deployment. In an embodiment, the hollow tubing for forming outer sheath 228 may be a thin-walled metallic tubing, such as stainless steel tubing of, for e.g., 316L. In another embodiment, the hollow tubing for forming outer sheath 228 may be formed from polymeric tubing having a reinforced metallic braided layer extending there through, such as the tubing shown and described in U.S. Pat. No. 5,755,714 to Lunn, which is incorporated by reference herein in its entirety.

Figure 3:
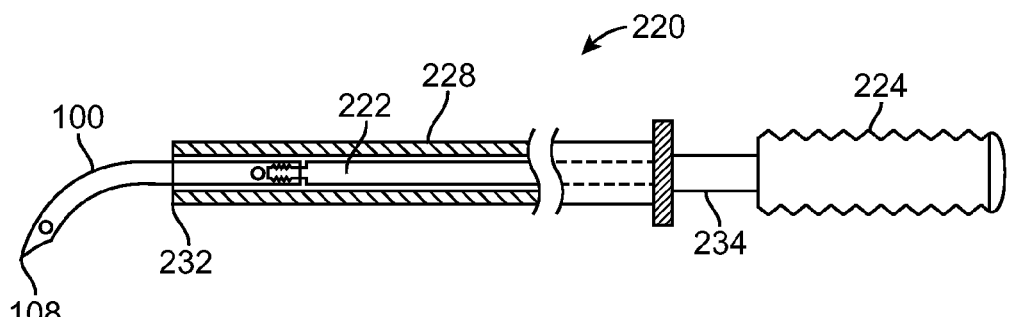
FIG. 3 shows the delivery system of FIG. 2 with the arteriovenous shunt partially exposed.
Figure 4:
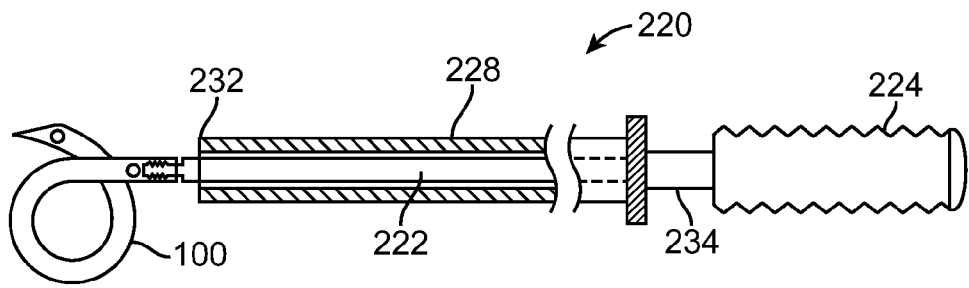
FIG. 4 shows the delivery system of FIG. 2 with the arteriovenous shunt fully exposed and returned to a spiral configuration.

FIG. 3 shows delivery system 220 of FIG. 2 with arteriovenous shunt 100 partially exposed or deployed. In order to expose or deploy shunt 100 from distal end 232 of delivery system 220, a clinician proximally retracts outer sheath 228 by pulling proximal end 230 while holding steady push rod 222 via handle 224 so that relative movement between outer sheath 228 and push rod 222 results in shunt 100 being released from the confinement of outer sheath lumen 226. In FIG. 3, the portion of shunt 100 that is released from outer sheath 228 has assumed its preset spiral configuration such that piercing end 108 of shunt 100 is substantially transverse to the longitudinal axis of delivery system 220. In FIG. 4, shunt 100 is shown fully exposed and returned to its preset spiral configuration.

Figure 5:
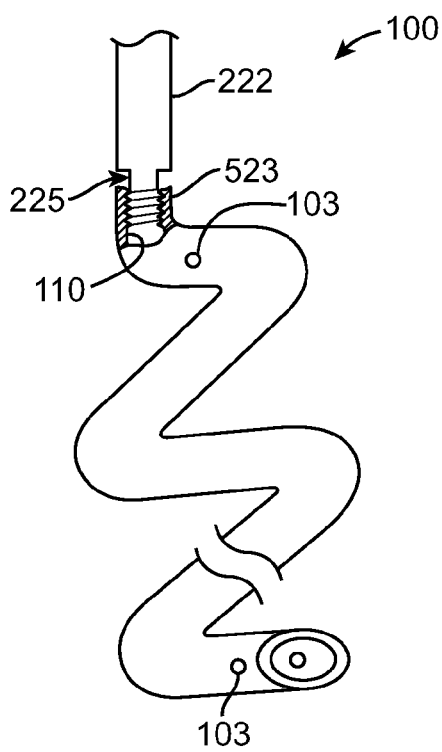
FIG. 5 is a partial sectional view showing the connection between the arteriovenous shunt of FIG. 1 and a push rod of the delivery system shown in FIGS. 2-4.

FIG. 5 is a partial sectional view of the connection between shunt 100 and push rod 222 of delivery system 220. Distal end 225 of push rod 222 includes external screw threads 523 that mate with internal screw threads 111 of attachment end 106 of shunt 100. In an embodiment, clockwise rotation of shunt 100 relative to push rod 222 tightens or connects shunt 100 to push rod 222, whereas counterclockwise rotation of shunt 100 relative to push rod 222 loosens or disconnects shunt 100 and push rod 222. It would be understood by one of skill in the art that this relationship could be reversed, i.e., tightened by counterclockwise rotation and loosened by clockwise rotation, without departing from the scope of the present invention. In embodiments hereof, the direction of rotation that tightens or connects shunt 100 to push rod 222 corresponds to the direction of the spiral of windings 104 such that rotating push rod 222 to turn or "corkscrew" shunt 100 through the vessel walls will tighten or maintain the threaded connection. With reference to the embodiment shown in FIGS. 1 and 5, windings 104 of shunt 100 spiral in a counterclockwise direction such that counterclockwise rotation of shunt 100 corkscrews shunt 100 through the vessel wall as well as tightens shunt 100 to push rod 222. In the alternate embodiment shown in FIG. 6, windings 604 of shunt 600 spiral in a clockwise direction such that clockwise rotation of shunt 600 corkscrews shunt 600 through the vessel wall as well as tightens shunt 600 to a push rod of a delivery device.

Figure 12:
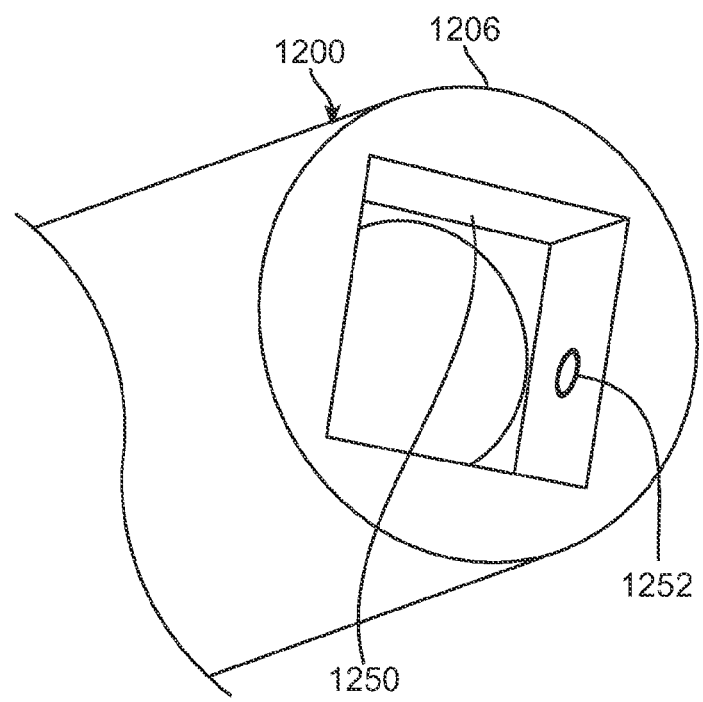
FIGS. 12 and 13 are perspective views of end portions of an arteriovenous shunt and a push rod of a delivery system, respectively, showing an alternative connection therebetween in accordance with another embodiment hereof.
Figure 13:
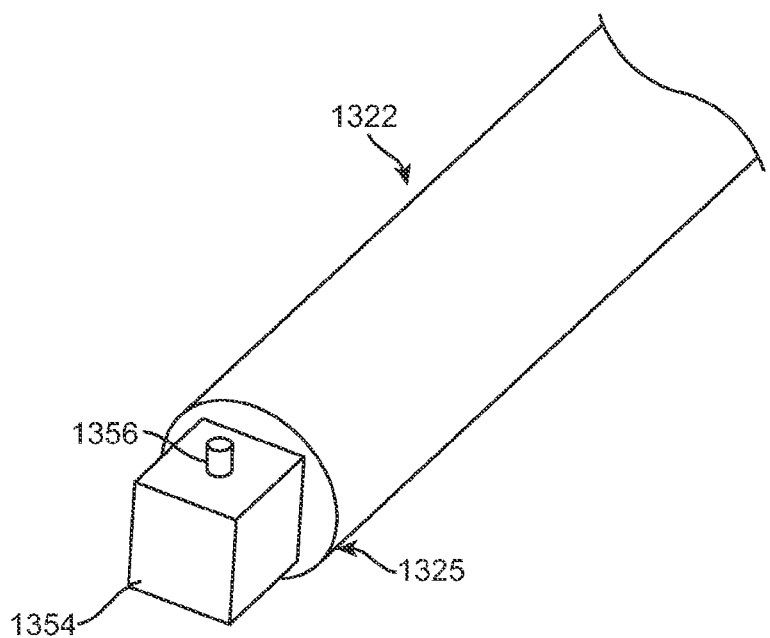

FIGS. 12 and 13 are perspective views of attachable end portions of an arteriovenous shunt 1200 and a push rod 1322 of a delivery system, respectively, showing an alternative releasable connection therebetween in accordance with another embodiment hereof. Shunt 1200 and push rod 1322 have similar features as previously described with respect to the other embodiments except that instead of a screw thread connection therebetween shunt 1200 includes a slot 1250 within attachment end 1206 for receiving a mating keyed portion 1354 that extends from distal end 1325 of push rod 1322. In the embodiment shown in FIGS. 12 and 13, shunt slot 1250 is a substantially square recess that is sized to receive push rod keyed portion 1354, which is of a substantially corresponding square shape. In order to lock shunt 1200 and push rod 1322 together to prevent longitudinal movement therebetween, shunt slot 1250 includes a locking pin recess 1252 in a longitudinally-extending side wall thereof for receiving a retractable locking pin 1356 that radially extends from push rod keyed portion 1354. Shunt 1200 is loaded onto the delivery system having push rod 1322 by aligning push rod keyed portion 1354 with shunt slot 1250 such that locking pin 1356 aligns with and slips into locking pin recess 1252. Push rod 1322 defines a lumen extending there through that accommodates a linkage or cord mechanism that may be manipulated by a clinician for retracting the push rod locking pin 1356 from the shunt locking pin recess 1252 to permit the release of shunt 1200 from push rod 1322 after shunt 1200 has been properly positioned between artery A and vein V as described in detail below.

Figure 6:
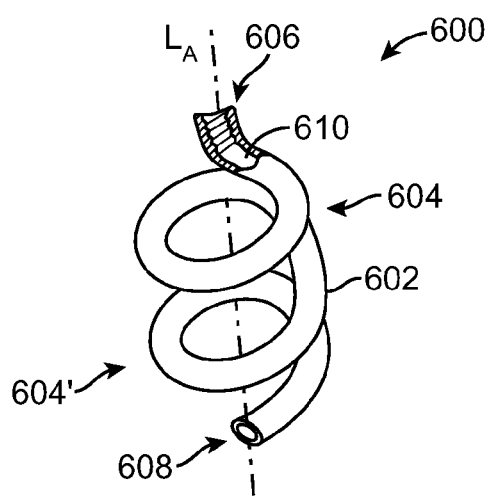
FIG. 6 is a partial sectional view of an arteriovenous shunt in accordance with another embodiment hereof.
Figure 6A:
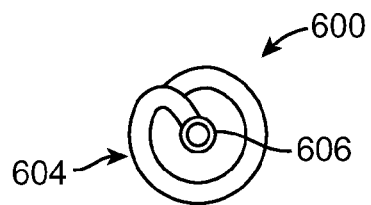
FIG. 6A is an end view of the arteriovenous shunt shown in FIG. 6.

FIGS. 7-10 illustrate a prophetic method of creating an artificial arteriovenous fistula between an artery A and an adjacent or vein V in accordance with an embodiment hereof utilizing spiral shunt 600 of FIG. 6 and delivery system 220. In an embodiment, artery A and vein V may be a femoral artery and an adjacent femoral vein. Initially shunt 600 is screwed onto push rod 222 of delivery system 220 and outer sheath 228 is slid over shunt 600 to hold shunt 600 in a straightened delivery configuration within distal end 232 as described above. With reference to FIG. 7, delivery system 220 having shunt 600 loaded therein is passed through an introducer sheath 740, which has been previously placed through the patient's skin S and underlying tissues to provide access to the treatment site as would be understood by one of ordinary skill in the art.

FIGS. 8-10 are cross-sectional views of artery A and vein V taken along line A-A of FIG. 7 and illustrate delivery system 220 delivering shunt 600 to fluidly connect artery A and vein V via fluid passageway 610 of shunt 600, thereby creating an artificial arteriovenous fistula between artery A and vein V. Ultrasound may be used to visualize entry of outer sheath 228 within artery A and subsequent positioning of shunt 600 between artery A and vein V. In FIG. 8, delivery system 220 and more particularly outer sheath 228 is shown transversely inserted through a wall of artery A via a first location or access point 842 therein. Access point 842 may be a path or opening in the wall of artery A previously made by, e.g., the well-known Seldinger percutaneous technique including introducer sheath 740, or by direct puncture with a trocar or a needle. Alternatively, distal end 232 of outer sheath 228 may be pushed through the arterial wall to provide access point 842. Distal end 232 of outer sheath 228 may be blunt, as shown, or sharpened in order to facilitate puncture of the arterial wall. Outer sheath 228 is shown in FIG. 7 approaching artery A at substantially a 90° angle to the longitudinal axis of artery A. In other embodiments, the outer sheath of the delivery device may approach the blood vessel at a 30° to 120° angle with respect to the longitudinal axis of the vessel depending on the location of the treatment site in the anatomy in which the spiral shunt is to be deployed.

Outer sheath 228 of delivery system 220 is proximally retracted to expose at least piercing end 608 of shunt 600. Shunt piercing end 608 is then advanced into contact with a second location or exit point 944 on the arterial wall substantially opposing access point 842 and push rod 222 is rotated via handle 224 to pierce the artery wall with shunt piercing end 608 and to corkscrew shunt 600 through the artery wall at exit point 944. As noted above, attachment end 606 of shunt 600 is substantially located along the central or longitudinal axis of shunt 600 to provide ease of rotation of shunt 606 by push rod 222 while shunt 600 is being corkscrewed through the vessel walls.

In FIG. 9 outer sheath 228 is shown further proximally retracted to fully expose shunt 600. Push rod 222 is shown further advanced and rotated such that shunt piercing end 608 has pierced the vein wall at an access point 946 adjacent to exit point 944 of the artery wall and shunt 600 is corkscrewed through the vein wall. In another embodiment, outer sheath 228 may be proximally retracted such that shunt 600 is fully exposed and in its spiral configuration prior to rotation and advancement of shunt 600 through the artery wall.

Once shunt 600 is properly positioned between artery A and vein V, push rod 222 of delivery system 220 is rotated in a direction to unscrew push rod 222 from shunt 600, thereby releasing shunt 600 from delivery system 220 and unplugging proximal fluid port 606. In this manner, shunt 600 is deployed to fluidly connect the lumens of artery A and vein V. In FIG. 10 delivery system 220 is shown being proximally refracted from artery A with attachment end or proximal port 606 of shunt 600 being positioned within the lumen of artery A and with piercing end or distal port 608 of shunt 600 being positioned within the lumen of vein V. Due to the spiral shape of shunt 600 no other securing means is necessary to maintain shunt 600 in position between artery A and vein V. Although shunt 600 is shown deployed between the vessels with a proximal end winding 604 positioned within artery A and a distal end winding 604' positioned within vein V, in other embodiments in accordance herewith fewer or more windings may be positioned in one or both of artery A and vein V as long as the attachment and piercing ends of the shunt are positioned in the artery and vein, respectively. Blood flow will proceed between artery A and vein V through shunt fluid passageway 610 due to a pressure gradient between the blood in the arterial system and the blood in the venous system. The method so described results in shunt 600 creating an artificial arteriovenous fistula between the two vessels. In another embodiment, an arteriovenous spiral shunt may be placed in accordance with the foregoing method from a vein to an artery if the patient's anatomy presents in such a manner.

Figure 11:
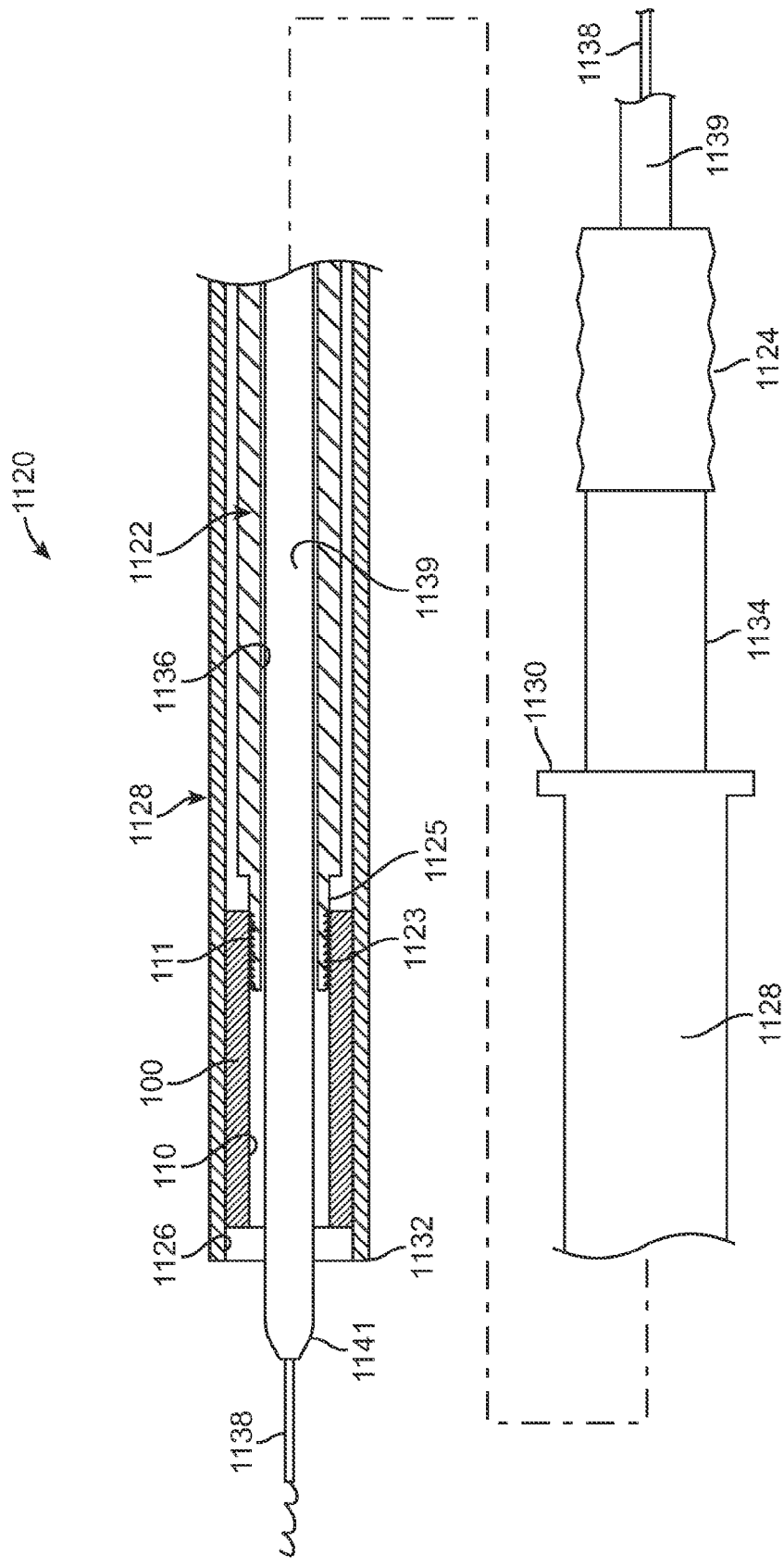
FIG. 11 is a partial sectional view of a delivery system in accordance with another embodiment hereof with the arteriovenous shunt of FIG. 1 held in a straightened delivery configuration therein.

FIG. 11 is a partial sectional view of delivery system 1120 in accordance with another embodiment hereof with arteriovenous shunt 100 of FIG. 1 held in a straightened delivery configuration therein. Delivery system 1120 includes similar structures and functions as delivery system 220 described above with the additional feature of having lumen 1136 extending through shaft portion 1134 and handle 1124 of push rod 1122 such that dilator 1139 and/or guidewire 1138 may be slidably disposed therein. Outer sheath 1128 has proximal end 1130 and distal end 1132 with an elongated tubular body defining lumen 1126 therebetween that is sized to slidably contain shunt 100 and push rod 1122 therein. Internal threads 111 of spiral shunt 100 mate with corresponding external threads 1123 on push rod distal end 1125 such that shunt fluid passageway 110 is in fluid communication with push rod lumen 1136 for slidably receiving dilator 1139 and/or guidewire 1138 there through. Dilator 1139 has a tubular body that extends from a proximal end (not shown) outside the patient for manipulation by a clinician to a tapered distal tip 1141 and defines a guidewire lumen (not shown) that slidably receives guidewire 1138 there through. Dilator 1139 may be formed from any suitable biocompatible polymeric or metallic tubing as would be understood by one of ordinary skill in the art.

Delivery system 1120 may be particularly suited for initially accessing an artery via the Seldinger technique mentioned above. In a method in accordance with an embodiment hereof, the artery first may be punctured with a trocar, which is a sharp hollow needle, with ultrasound guidance if necessary to create a pathway from the skin level through the subcutaneous tissue layers and through a location in the artery wall, such as access point 842 in FIG. 8. Guidewire 1138 may then be advanced through the trocar, and the trocar may then be withdrawn. Dilator 1139 may then be slid over guidewire 1138 such that tapered distal tip 1141 passes through and enlarges the pathway through the artery wall created by the trocar. Delivery system 1120 may then be advanced over dilator 1139, such that outer sheath distal end 1132 passes through and further enlarges the pathway through the artery wall. Once outer sheath distal end 1132 is appropriately positioned within the artery lumen, dilator 1139 and guidewire 1138 are withdrawn from the patient. In an embodiment, dilator 1139 may be omitted such that delivery system 1120 is advanced over guidewire 1138 to enlarge the pathway through the artery wall that was initially created by the trocar. Ultrasound or fluoroscopy may be used to confirm the position of delivery system 1120 and to aid in manipulating delivery system 1120 to the desired location. Delivery system 1120 may then be used to deploy shunt 100 between the artery and an adjacent vein in the manner previously described and illustrated with reference to the embodiment of FIGS. 6-10.

In most patients, arteriovenous spiral shunts in accordance with embodiment hereof are intended to be implanted on a temporary basis. Accordingly, in the event that, e.g., spiral shunt 600 is no longer needed, shunt 600 may be surgically removed. In another embodiment, shunt 600 may be left in the patient with blood flow therethrough blocked by an occlusion device such as an embolization coil, which may be inserted into shunt fluid passageway 610 via an intravascular procedure. In another embodiment where a shunt 1200 is used with a delivery system having the connection shown in FIGS. 12 and 13, push rod 1322 of the delivery system may be re-introduced into artery A and push rod keyed portion 1354 may be re-aligned with shunt slot 1250 such that locking pin 1356 aligns with and slips into locking pin recess 1252 to enable push rod 1322 and shunt 1200 to be re-attached for removal of the shunt from the patient's body. Fluoroscopy may be used to aid a clinician in aligning the threads of the two components.

A reduction in blood pressure and improvement of blood oxygenation are measures of the efficacy of an implanted arteriovenous spiral shunt in accordance with embodiments hereof. If a further reduction in blood pressure or improvement of blood oxygenation is warranted, an additional arteriovenous spiral shunt may be implanted in the vicinity of the earlier implanted shunt or in another part of the body by methods in accordance herewith. For example, a spiral shunt 100 having a fluid passageway 110 of a 2 mm diameter may be implanted between the femoral artery and femoral vein of the patient's right leg after which the patient's blood pressure and/or blood oxygenation may be measured to determine changes therein due to the creation of the artificial arteriovenous fistula. If it is determined by one or more of the patient's measurements that an additional arteriovenous fistula is necessary or desirable, then a second spiral shunt 100 having fluid passageway 110 of a 2 mm or other diameter may be implanted between the femoral artery and femoral vein of the patient's right leg near the first spiral shunt 100. Alternatively, the second spiral shunt 100 may be placed at another location in the body, such as between the femoral artery and femoral vein of the patient's left leg. The patient's blood pressure and/or blood oxygenation may be measured again to determine changes therein due to the creation of the second arteriovenous fistula and a determination may then be made whether an additional arteriovenous fistula is necessary or desirable, and so on. In this manner, incremental clinical improvements of the patient's condition may be made by sequential implantation of shunts that can be expected to be safer for a particular patient than trying to predict an optimum size of a single shunt, which carries a risk that the single shunt may be too large.

While various embodiments according to the present invention have been described above, it should be understood that they have been presented by way of illustration and prophetic example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of creating an artificial arteriovenous fistula between an artery and an adjacent vein of a patient comprising the steps of:
   inserting a distal end of a delivery device transversely through a first location on a wall of the artery into a lumen thereof;
   exposing at least a piercing end of a hollow spiral shunt from the distal end of the delivery device within the lumen of the artery, wherein the spiral shunt defines a fluid passageway between proximal and distal ports thereof;
   rotating and distally advancing the delivery device to pierce the artery wall at a second location generally opposite the first location with the spiral shunt piercing end;
   after piercing the artery wall at the second location, rotating and distally advancing the delivery device to pierce a wall of the adjacent vein with the spiral shunt piercing end; wherein during the step of rotating and distally advancing the delivery device, the spiral shunt is corkscrewed through the wall of the artery and the wall of the vein; and
   releasing the spiral shunt from the delivery device such that the proximal port of the spiral shunt resides within the artery lumen and the distal port of the spiral shunt resides within a lumen of the vein, wherein the fluid passageway of the spiral shunt forms the artificial arteriovenous fistula to permit blood flow between the artery and the vein.

2. The method of claim 1 further comprising the step of:
   loading the spiral shunt into the distal end of the delivery device by screwing the proximal end of the spiral shunt onto a push rod of the delivery device, wherein the push rod is slidably received within a tubular sheath of the delivery device, and sliding the tubular sheath relative to the push rod positions the spiral shunt within the distal end of the delivery device.

3. The method of claim 2, wherein the spiral shunt is held in a straightened configuration within the tubular sheath of the delivery device and wherein, during the step of exposing, the shunt returns to a preset spiral configuration as the tubular sheath is proximally withdrawn.

4. The method of claim 2, wherein the step of releasing the spiral shunt from the delivery device includes unscrewing the push rod from the spiral shunt.

5. The method of claim 1 further comprising the step of:
   puncturing the wall of the artery to provide an access point for inserting the delivery device through the wall of the artery.

6. The method of claim 5, wherein the step of puncturing is performed by pushing one of a trocar, an introducer sheath and the distal end of the delivery device through the wall of the artery.

7. The method of claim 1, wherein the spiral shunt includes at least two windings such that when the spiral shunt is deployed between the artery and the vein at least a proximal end winding of the spiral shunt is positioned within the artery and at least a distal end winding of the spiral shunt is positioned within the vein.

8. The method of claim 1, wherein the artificial arteriovenous fistula between the artery and vein is created for treating a patient with chronic obstructive airway disease or complications thereof.

9. The method of claim 8, further comprising:
   creating a second arteriovenous fistula in accordance with the method of claim 1.

10. The method of claim 9, wherein the second arteriovenous fistula is created between the same artery and vein as the first arteriovenous fistula.

11. The method of claim 9, wherein the second arteriovenous fistula is created between a different artery and vein than the first arteriovenous fistula.

* * * * *